(12) United States Patent
Diekmann (10) Patent No.: US 9,435,781 B2
(45) Date of Patent: Sep. 6, 2016

(54) GAS DETECTION DEVICE

(71) Applicant: Dräger Safety AG & Co. KGaA, Lübeck (DE)

(72) Inventor: Wilfried Diekmann, Utecht (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/614,710

(22) Filed: Feb. 5, 2015

(65) Prior Publication Data

US 2015/0226719 A1    Aug. 13, 2015

(30) Foreign Application Priority Data

Feb. 8, 2014   (DE) .................... 10 2014 001 700

(51) Int. Cl.
| | |
|---|---|
| *G01N 21/00* | (2006.01) |
| *G01N 33/00* | (2006.01) |
| *G01N 21/55* | (2014.01) |
| *G01N 21/3504* | (2014.01) |
| *G01N 21/01* | (2006.01) |

(52) U.S. Cl.
CPC .......... *G01N 33/0073* (2013.01); *G01N 21/01* (2013.01); *G01N 21/3504* (2013.01); *G01N 21/55* (2013.01); *G01N 33/0027* (2013.01); *G01N 2021/3513* (2013.01); *G01N 2201/02* (2013.01); *G01N 2201/021* (2013.01); *G01N 2201/061* (2013.01)

(58) Field of Classification Search
CPC ............. G01N 33/84; G01N 21/3504; G01N 33/4925; G01N 19/04; G01N 2021/3513; G01N 21/01; G01N 21/17; G01N 21/532; G01N 21/55; G01N 21/95; G01N 21/954; G01N 2201/02; G01N 2201/021; G01N 2201/023

See application file for complete search history.

(56) References Cited

U.S. PATENT DOCUMENTS

| | | | |
|---|---|---|---|
| 4,496,416 A | * | 1/1985 | Machler .................... G01J 3/02 156/293 |
| 5,880,354 A | | 3/1999 | Newman et al. |
| 8,399,839 B2 | | 3/2013 | Hüttmann et al. |

FOREIGN PATENT DOCUMENTS

| | | |
|---|---|---|
| DE | 199 40 280 A1 | 3/2001 |
| DE | 100 58 469 C1 | 5/2002 |
| DE | 10 2012 007561 A1 | 10/2013 |

OTHER PUBLICATIONS

British Combined Search and Examination Report of Jun. 30, 2015.

* cited by examiner

*Primary Examiner* — Michael P Stafira
(74) *Attorney, Agent, or Firm* — McGlew and Tuttle, P.C.

(57) ABSTRACT

A gas detection device with at least one functional device (1), which is fixed to a platform, is pivotable about at least two pivot axes (2, 3) relative to the platform. The functional device (1) is designed to emit and/or receive or reflect radiation that is analyzably variable due to the presence of a gas to be detected. The gas detection device has an adjusting device (9), which has a fixing device for temporary fixation to the platform and an application device for the defined application on the functional device (1) of forces that lead to a pivoting about the pivot axes (2, 3). The application device acts detachably on the functional device (1).

20 Claims, 5 Drawing Sheets

GAS DETECTION DEVICE

CROSS REFERENCE TO RELATED APPLICATIONS

This application claims the benefit of priority under 35 U.S.C. §119 of German Patent Application DE 102014001700.1 filed Feb. 8, 2014, the entire contents of which are incorporated herein by reference.

FIELD OF THE INVENTION

The present invention pertains to a gas detection device, which comprises a functional device fixed to a platform and pivotable about at least two pivot axes.

BACKGROUND OF THE INVENTION

Gas detection devices are used, for example, in units for delivering and processing combustible and/or toxic gases in order to detect gases released in an unintended manner.

Gas detection devices that measure the concentration of harmful substances locally, i.e., in the immediate surrounding area, and are usually interlinked with one another in order to make it possible to monitor larger areas, are known.

There also are gas detection devices with an open measuring section, which are called open-path gas detection devices. The measuring section may range from a few m to a few hundred m. Open-path gas detection devices analyze electromagnetic or light radiation, which has passed through a defined monitoring range. The electromagnetic or light radiation is analyzed with respect to a possible interaction with a gas being released in an unintended manner, which is associated with a change in the properties of the radiation. This makes possible the continuous monitoring of a relatively large monitoring area with respect to an unintended release of gas, and the quantity and the species of the gas or gases being released can also be inferred from an analysis of the altered properties of the radiation. The radiation used for the monitoring may be, for example, thermal radiation of the background, or this radiation originates from a source of the gas detection device itself.

The functional devices used in gas detection devices have, as a rule, a limited field of view, i.e., these must be oriented relatively accurately towards the radiation source or the area to be monitored. This also applies to open-path gas detection devices, which comprise as functional devices, as a rule, at least one transmitter with a radiation source and a receiver with a radiation detector, to which the radiation emitted by the radiation source is focused. The radiation source may be, for example, a thermal radiator, for example, a xenon flash lamp, or a semiconductor radiator, for example, a tunable laser. Such open-path gas detection devices require orientation of both the transmitter and the radiation source integrated therein in order to direct a sufficient amount of radiation output to the inlet aperture of the receiver and the receiver in order for the radiation falling on the inlet aperture to reach the radiation detector as centrally as possible.

Another type of open-path gas detection device comprises a reflector, which is positioned at a distance of usually up to 50 m from a combined transmitter/receiver unit and onto which the radiation emitted by a radiation source is projected. The reflector reflects the radiation in the direction of the transmitter/receiver unit, as a result of which this can be detected by a radiation detector of the unit.

Another type of an open-path gas detection device is the so-called gas camera, whose spectral sensitivity is set to the absorption bands of a gas and which makes the gas being released from a leak visible or recognizes that gas by means of image processing and sends a warning signal.

Dräger Safety AG & Co. KGaA commercially offers an open-path gas detection device, in which both the transmitter and the receiver are connected with a baseplate by means of a joint arrangement each, which forms two pivot axes directed at right angles to one another. The joint arrangement is designed such that the two pivot axes intersect the optical axis of the radiation source and of the radiation receiver, respectively, approximately in the center of the housing of the respective functional device. Eight locking screws, four for the transmitter and four for the receiver, must be loosened and tightened after orientation to orient the transmitter or the receiver. The orientation itself is performed manually and can be checked by means of crosshairs, which is represented graphically on a hand-held device. A minimum signal is necessary for the analysis for displaying the crosshairs, so that a coarse orientation must be performed prior to the fine orientation by an optical direction finding, which can be carried out with the support of a telescope, which must be fastened to the housing of the transmitter or receiver in a defined manner. Once the orientation has been performed, the locking screws are tightened, so that the orientation is maintained unchanged for a rather long time period. Fine adjustment with strong holding force is advantageous for the accuracy of the orientation and for preserving the angle when tightening the locking screws.

Some open-path gas detection devices have adjusting screws with fine thread, which are used to orient the transmitter or the receiver with the locking screws loosened and transmit the translatory component of the screw motion to the transmitter or receiver in the process. As a consequence of the small pitch of the thread, accurate orientability of the transmitter and receiver can be achieved with these. If the adjusting screws are also used as locking screws at the same time, strong holding forces can, moreover, be brought about with these. This is especially advantageous when the adjusting/locking screws are arranged comparatively close to the respective axes of rotation. Adjusting or locking screws with fine thread are less suitable for use in an industrial environment because of the stresses due to contamination and corrosive media that are associated with them.

SUMMARY OF THE INVENTION

Based on this state of the art, a basic object of the present invention is to provide an advantageous possibility for orienting an open-path gas detection device.

According to the invention, a gas detection device is provided comprising a functional device comprising at least one of a radiation emitter, a radiation receiver and a radiation reflector. The radiation varies in an analyzable manner due to a presence of a detectable gas. A pivot mount arrangement is provided mounting the functional device pivotably to a support platform for pivoting about at least two pivot axes relative to the platform. An adjusting device is provided comprising a fixing device for a temporary fixation of the adjusting device relative to the platform and an application device for a defined application of forces to the functional device that lead to a pivoting of the functional device about the pivot axes.

The basic idea of the present invention is to carry out the exact orientation of a functional device, i.e., of a transmitter or of a receiver or of a combined transmitter/receiver unit or optionally of a reflector, which orientation is necessary for the correct function of an (open-path) gas detection device, by means of an adjusting device, which is connected with the respective functional device for the process of orientation only.

A gas detection device according to the present invention correspondingly comprises at least one functional device, which is fixed to a platform, is pivotable about at least two pivot axes relative to the platform and is designed to emit and/or receive or reflect an oriented radiation, which is analyzably variable due to the presence of a gas to be detected, and additionally an adjusting device, which has fixing means for temporary fixation to the platform and an application device for the defined application to the functional device of forces that lead to a pivoting about the pivot axes, wherein the application device is detachably connected to the functional device.

"Connected" is defined here such that the adjusting device cooperates with the platform or the functional device such that at least the transmission of the forces provided for pivoting the functional device about the pivot axis can take place.

The "platform" is a structure (designed such that it is immobile in relation to the intended detection area) to which the functional device can be or is permanently or detachably fixed. It may be, for example, a wall or an earth-fixed ground structure (e.g., a ground surface or a post anchored in the ground) or a baseplate that can be fastened to a wall or to an earth-fixed ground structure. A platform in the form of a stand that can be erected on the ground, e.g., a tripod.

The detachability according to the present invention of the adjusting device from the rest of the gas detection device makes it possible, on the one hand, to use an individual adjusting device for a plurality of functional devices, as a result of which the total costs for a gas detection device having a plurality of functional devices and/or for a gas detection system comprising a plurality of gas detection devices can be kept low. In addition, provisions may advantageously be made for the fixing device not to remain at a functional device of the gas detection device over a longer period of time. This makes it possible to design the adjusting device, regardless of the requirements that are dictated by a necessary long-term functionality in an environment characterized by adverse conditions, especially highly contaminated and/or highly corrosive environment, even though the gas detection device is intended, in principle, for use in such an environment. Construction details that are not suitable for long-term use in such an environment characterized by such adverse conditions can thus be implemented in the adjusting device. In particular, a relatively precise orientation mechanism can thus be used, whose components may be expensive and do not have to be suitable for long-term use in an environment characterized by adverse conditions.

Since the adjusting device is not preferably intended to remain permanently on the functional device, devices should be additionally provided for securing an orientation of the functional device set by means of the adjusting device. These may be integrated especially in pivot bearings (forming the pivot axes). In particular, these devices for securing an orientation may act in a non-positive manner and/or be based on fixing screws integrated in the pivot bearing. Provisions may, in this case, be made for the devices to be designed such that even during the orientation by means of the adjusting device, these generate a frictional resistance, which is so high that the orientation set is maintained after removal of the adjusting device. As an alternative, these may, however, also be designed such that these bring about only comparatively low frictional resistances during the orientation and are tightened only after completion of the orientation of the functional device (but with the adjusting device not yet removed).

The (open-path) gas detection device is preferably designed such that this has a first functional device, designed to emit the radiation, i.e., a transmitter, and a second functional device designed to receive the radiation, i.e., a receiver, which are each fixed to a platform and are provided at a defined distance (e.g., between about 4 m and about 200 m) for positioning in which they are oriented towards each other. Both functional devices may be preferably designed to be oriented by means of the same adjusting device, and to form for this the same connection points for the adjusting device.

However, the use of the adjusting device, which is detachable according to the present invention, is also advantageous in such an (open-path) gas detection device in which the functional device is designed to emit and to receive the radiation, i.e., as a transmitter/receiver unit, and, moreover, a reflector, which can be positioned independently from this functional device, is present (as a second functional device). Provisions may advantageously be made in case of such a design of the detection device as well to design both functional devices for being oriented by means of the same adjusting device, and to form the same connection points for the adjusting device for this.

An especially exact orientation of the functional device or of one of the functional devices can be achieved if the pivot axes are directed at right angles to one another. These may be oriented vertically and horizontally (in the position of the platform that is intended for the operation of the gas detection device).

Furthermore, provisions may advantageously be made for the application device to be designed such that the lines of application of the forces that can be generated by the application device are directed at right angles to one of the pivot axes. All the forces generated by the application devices can thus be used for the pivoting of the functional device, which pivoting brings about the orientation about the at least two pivot axes. Force components that are oriented in the direction of the pivot axes are largely avoided hereby, as a result of which stressing of the pivot bearings with these force components is, moreover, avoided. The pivot bearings may as a result possibly be dimensioned as relatively weak pivot bearings, as a result of which costs can be saved.

Provisions may be made in a preferred embodiment of the gas detection device according to the present invention for the application devices to be designed such that the lines of application of the forces that can be generated by these are located at the greatest possible distance of especially between 10 mm and 300 mm from the respective corresponding pivot axis. A comparatively high torque can thus be generated with comparatively weak forces. It may also be advantageous that as a consequence of the great distance, relatively large motions of the application devices lead to an only relatively small rotation of the functional device. A sufficiently precise orientation of the functional device may possibly be achieved as a result with an application device working relatively imprecisely and/or with a largely dimensioned application device. For example, designing the application device with a fine thread can be eliminated in case of an application device that is designed in the form of an adjusting screw.

Provisions may be made in another preferred embodiment of the gas detection device according to the present invention for the adjusting device to comprise a first carriage guided displaceably in a stand by a first adjusting element and a second carriage guided displaceably by a second adjusting element on the first carriage. This is an embodiment of the adjusting device with a simple design, with which exact adjustment paths of the application device can, moreover, be achieved along with easy handling. The adjusting elements may be designed, for example, as adjusting screws in a cost-effective manner.

An embodiment of the adjusting device with an especially simple design can be obtained if the application device comprises at least one pair and preferably two pairs of adjusting elements, especially adjusting screws, which act on opposite sides of the detection device. A precise orientation of the functional device can be achieved by simultaneous, opposite adjustment of the pairs of adjusting elements.

Besides cost-effective adjusting elements in the form of adjusting screws, the application device may preferably (also) have adjusting actuators, which make it possible to orient the functional device even without manual action. As a result, it is possible to create especially a gas detection device that can be oriented fully automatically. This may also have for this a control device for determining the adjusting deviation from a desired orientation. This control device may then be connected with the adjusting actuators of the application device in a signal-carrying manner and designed for automatic orientation of the functional device as a function of the adjusting deviation determined.

The adjusting actuators may be designed, for example, in the form of electric stepper motors, servomotors, motor/gear combinations and/or piezo motors. Pneumatic or hydraulic actuators may be used as well.

The adjusting actuators may be supplied with control signals by the control device. The adjusting deviation can be determined from a measurement of the intensity of the radiation output transmitted. If only this is available as an actuating variable, the control unit may have an algorithm, with which the orientation of the functional device that corresponds to the maximum radiation output can be determined. Such algorithms are known. If measured values concerning a deflection of the functional device from the optical axis are additionally available, a usual control algorithm, e.g., with a proportional-integral-differential component (PID controller) may also be sufficient.

The adjusting actuators and/or the control device can be supplied with energy via an energy supply unit intended for the functional device (especially the radiation source and/or the detector) and/or a separate energy supply unit. A separate energy may be embodied by means of a supply line connected temporarily for connection to an electric supply network and/or by means of batteries.

The present invention will be explained in more detail below on the basis of exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
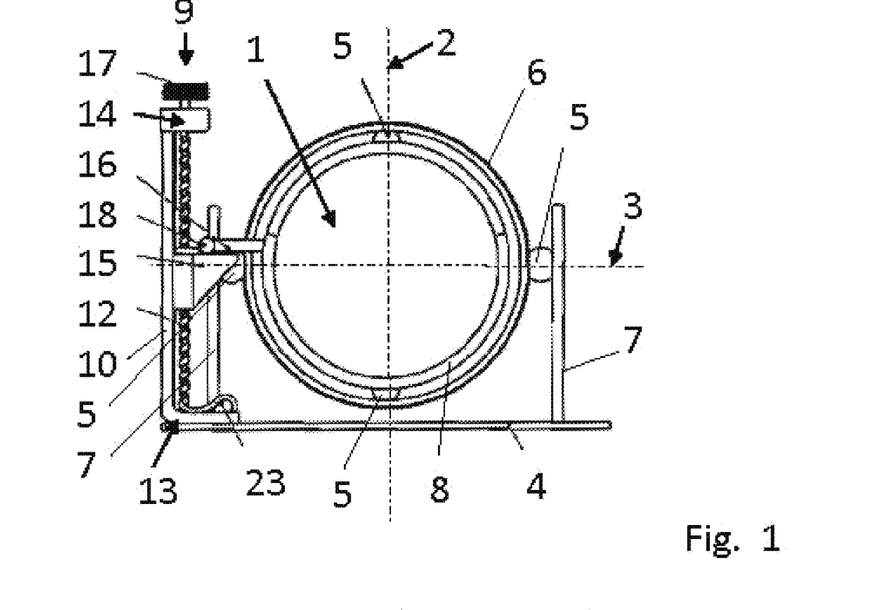
FIG. 1 is a front view of a first embodiment of a gas detection device according to the present invention.
Figure 2:
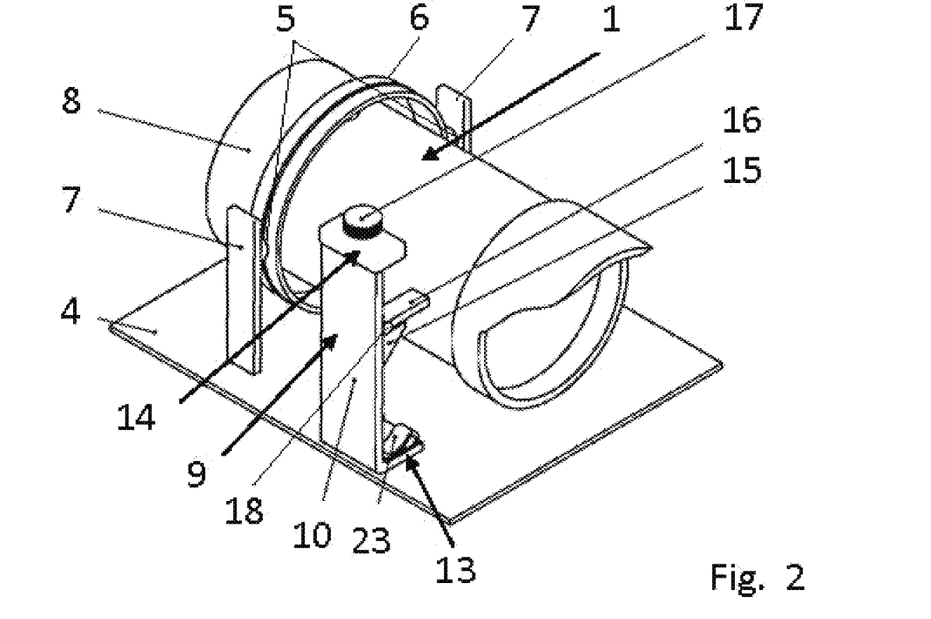
FIG. 2 is a perspective view of the gas detection device according to FIG. 1.
Figure 3:
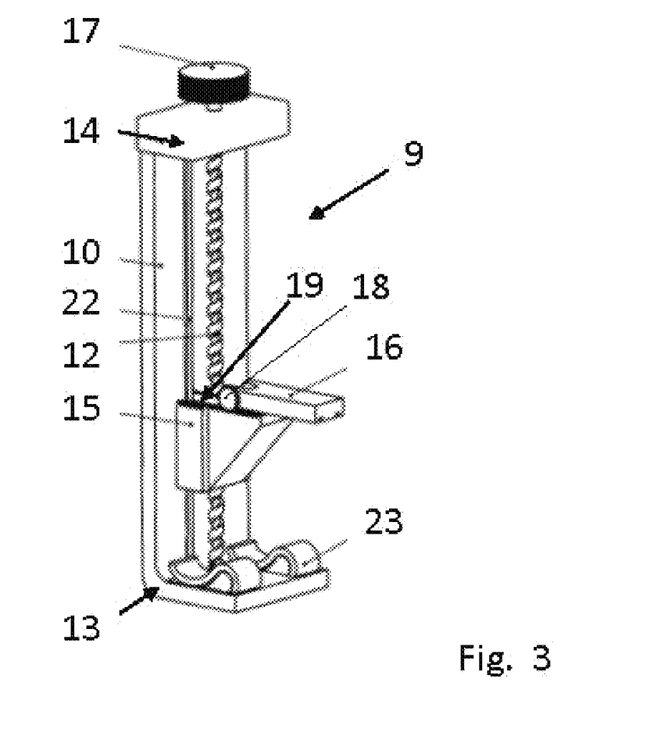
FIG. 3 is a perspective view of the adjusting device of the gas detection device according to FIGS. 1 and 2.

Referring to the drawings, the gas detection device of the invention comprises a detection unit shown in FIGS. 1 through 3 comprising a functional device 1, which is connected with a platform pivotably about two pivot axes 2, 3. The platform comprises a baseplate 4 and a mounting frame rigidly connected to it.

The mounting frame comprises a pivot bearing arrangement (pivot mount arrangement) 50 with two pairs of pivot bearings 5. The two pivot bearings 5 of each pair are arranged coaxially and form one of the pivot axes 2, 3 as a result. Via a first pair of pivot bearings 5, the functional device 1 is mounted rotatably about a first pivot axis 2, which is directed at right angles in the figures, within a bearing ring 6. The bearing ring 6 is mounted, in turn, between two beams 7 of the mounting frame via a second pair of pivot bearings 5 about the second pivot axis 3, which is directed at right angles to the first pivot axis 2. The functional device 1 can thus be pivoted, i.e., rotated within limits, relative to the bearing ring 6 about the first pivot axis 2 and together with this about the second pivot axis 3, but always relative to the baseplate 4 (and the beam 7). The pivot bearing arrangement permits a superposition of these two pivoting motions, so that the functional device 1 can be pivoted, in principle, in any desired directions.

The functional device 1 may be a transmitter, a receiver or a transmitter/receiver unit of the gas detection device. If it is a transmitter or a receiver, the gas detection device also comprises another functional device 1, which is not shown in the figures and which may be mounted corresponding to the functional device 1 shown. In particular, provisions may be made for the additional functional device 1 to differ only concerning the equipment with functional elements accommodated in a housing 8 of the functional device 1. While a functional device 1 designed as a transmitter has especially a radiation source for directed radiation, especially light radiation, for example, a xenon lamp or a laser, a functional device 1 designed as a receiver comprises especially a detector for the corresponding radiation. The two functional devices 1 are intended in this case for positioning at the two ends of a defined measuring section 120, in which case the most exact orientation possible in relation to one another, especially coaxiality of the optical axes of the radiation source and detector, shall be provided.

In addition, one or more computer units 110, which may act as control and/or analyzing devices, may be integrated in both types of functional devices 1. However, these computer units 110 may also be arranged outside the housing 8 of the functional device 1 and connected especially with the radiation source and the detector in a signal-carrying manner (in a wired or wireless manner).

The functional device 1 may be a transmitter/receiver unit, which thus comprises a radiation source and a corresponding detector and optionally a computer unit. Such a functional device 1 may be combined with a reflector 101, which is arranged at the corresponding other end of the defined measuring section and reflects radiation from the radiation source into the detector. This also requires the most exact orientation possible of the functional device 1 and of the reflector 101 in relation to one another.

The baseplate 4 is provided for being placed on or in contact with a ground surface or a wall. FIGS. 1-8 show an orientation of the gas detection device in case it is placed on a ground surface. The baseplate 4 may have a fastening device, which can be used for fastening on the ground surface (or a wall). The fastening device may be, for example, access openings, through which extend the screws that can be screwed with a thread formed or to be formed in the ground surface or a wall.

An adjusting device 9 of the gas detection device is connected with the baseplate 4, on the one hand, and with the housing 8 of the functional device 1, on the other hand. The adjusting device 9 comprises a stand 10, which is detachably connected with the baseplate 4 via a fastening device with one or more fastening elements. The fastening elements in the exemplary embodiment shown in FIGS. 1 through 3 are designed in the form of spring shackles 23, which are elastically deformed when sections of a foot 13 of the stand 10 are pushed into the gap formed between the spring shackles 23 and the top side of the baseplate 4, as a result of which the stand 10 is pressed against the baseplate 4 and is held on same.

Figure 4:
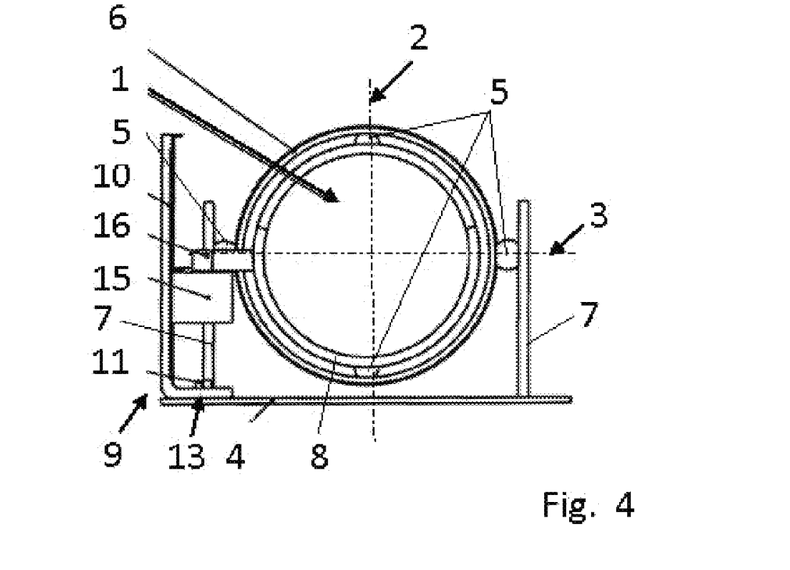
FIG. 4 is a front view of a second embodiment of a gas detection device according to the present invention.
Figure 5:
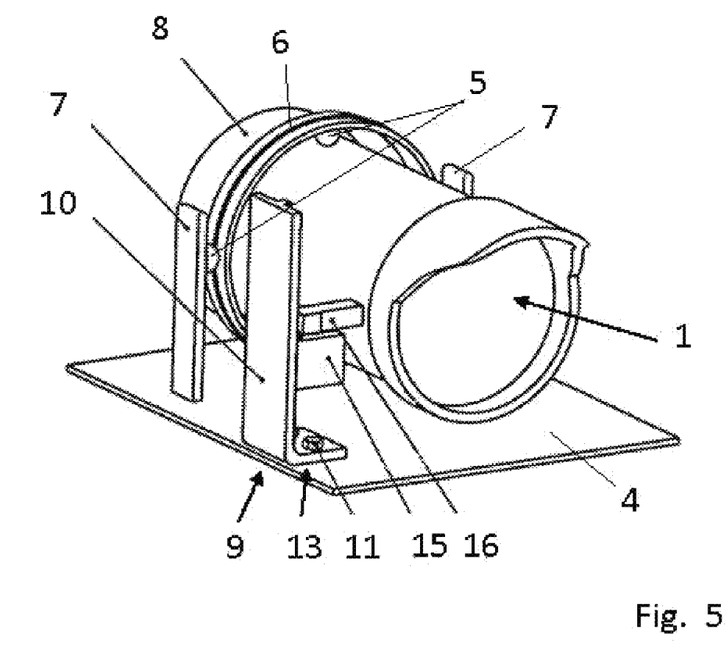
FIG. 5 is a perspective view of the gas detection device according to FIG. 4.
Figure 6:
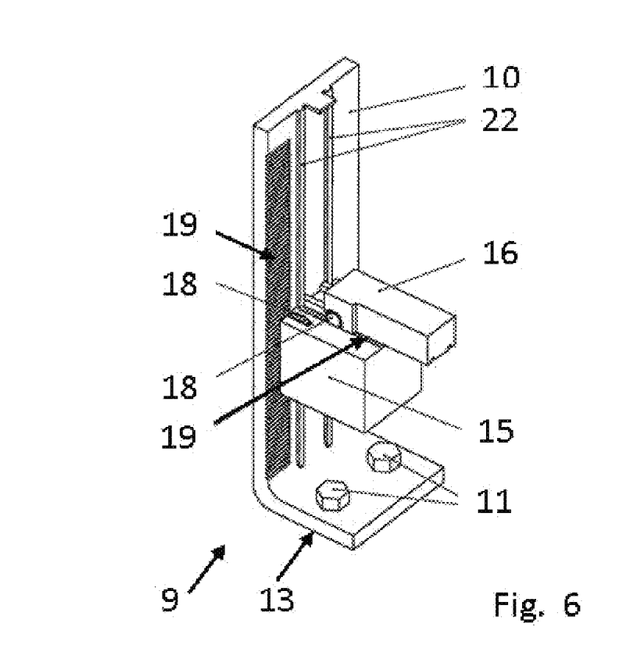
FIG. 6 is a perspective view of the adjusting device of the gas detection device according to FIGS. 4 and 5.

Alternative fastening elements, for example, fastening screws 11 extending through passage openings of the stand 10 and meshing with threads of the baseplate 4, as they are shown in the exemplary embodiment according to FIGS. 4 through 6, are equally possible. Threaded bolts, which are rigidly connected with the baseplate 4, extend through passage openings of the stand 10 and are screwed onto the nuts (not shown), may be provided as well.

An adjusting screw 12 or spindle is mounted rotatably in the foot 13 and a head 14 of the stand 10. The adjusting screw 12 cooperates with a first carriage 15 of the adjusting device 9 such that its rotation leads to a translatory displacement of the first carriage 15 along the longitudinal axis of the adjusting screw 12 and thus at right angles to (and at a spaced location from) the second pivot axis 3 of the bearing arrangement. The first carriage 15 is guided nonrotatably by a guide projection 22 of the stand 10, which meshes (engages) with a guiding groove of the first carriage 15.

A second carriage 16 is mounted movably on the first carriage 15, and a motion of the second carriage 16 is directed at right angles to a motion of the first carriage 15, which can be brought about by the adjusting screw 12, and thus at right angles to (and at a spaced location from) the first axis of rotation 2 of the bearing arrangement.

The end face of the second carriage 16 facing the functional device 1 contacts the housing 8 of the functional device 1 and is detachably connected with this via fasteners, not shown. The fastening device should be designed in this case such that these forces can be transmitted in all directions of motion made possible by the adjusting device 9 for the second carriage 16 thereof. The fastening device may be designed, for example, in the form of a screw connection.

Due to a rotation of the adjusting screw 12 brought about manually, the first carriage 15 can be displaced along the longitudinal axis of the adjusting screw 12, which leads to a partial rotation or a pivoting of the functional device 1 about this second pivot axis 3 as a consequence of the force-transmitting connection between the adjusting device 9 and the functional device 1 and the distance between the connection point and said second pivot axis 3. The adjusting screw 12 has a rotary knob 17 on the head side for this.

Displacement of the second carriage 16 on the first carriage 15 leads, by contrast, to a pivoting of the functional device (1) about the first pivot axis 2. The displacement of the second carriage 16 is likewise brought about by manual rotation of a rotary knob (not shown) in the exemplary embodiment according to FIGS. 1 through 3. This rotation is reduced via a gear mechanism mounted in the second carriage 16 to a toothed gear 18, which meshes with a toothed rack contour 19 of the first carriage 15. The gear mechanism is designed such that a displacement of the second carriage 16 is possible by turning the rotary knob, while a direct displacement of the second carriage 16 (and a turning of the rotary knob associated therewith), which is brought about by external forces, is prevented by a self-locking device.

Instead of the actuating drive of the second carriage 16, which is shown in FIGS. 1 through 3 and comprises a combination of the rotary knob, gear mechanism, toothed gear 18 and toothed rack contour 19, an adjusting screw (not shown), which is mounted rotatably in the first carriage 15 and cooperates with the second carriage 16, may also be provided for this second carriage 16.

By turning the two rotary knobs, the functional device 1 can be pivoted such that the desired orientation relative to the additional functional device 1, not shown here, is achieved. As soon as the desired orientation is achieved and secured, the adjusting device 9 can be separated from the baseplate 4 and the functional device 1, by loosening the fastening elements of the fastening device, and the adjusting device 9 can be removed. This adjusting device 9 is available in this case for orienting another functional device 1 of the said gas detection device or of another gas detection device, which said functional device 1 has corresponding interfaces for the adjusting device.

Securing of the orientation of the functional device 1, once achieved, can be achieved, for example, by means of fixing screws (not shown), which are integrated in the pivot bearing 5 and which are tightened in advance, before removal of the adjusting device 9 and increase the friction in the pivot bearings 5 to the extent that an unintended change in the set orientation is prevented in case of forces normally acting on the functional device during the operation of said functional device. Instead of fixing screws, it is also possible to use other fixing devices, especially quick-closing devices, for example, bayonet catches or tension levers. As an alternative, the pivot bearings 5 may also be designed such that these generate basically a relatively high frictional resistance, which can be overcome by the action of the adjusting device 9 without problems, but it prevents an unintended adjustment after removal of the adjusting device 9.

The second embodiment of a gas detection device according to the present invention shown in FIGS. 4 through 6 differs from the first embodiment according to FIGS. 1 through 3—besides in the type of the fastening elements for fastening the stand 10 on the baseplate 4—essentially only in respect to the adjusting elements used to displace the first carriage 15 and the second carriage 16. Electric adjusting actuators are used here. An electric servo motor (not visible) each, whose drive shafts are connected directly or indirectly with a respective toothed gear 18 for rotation in unison, and which mesh with toothed rack contours 19 of the stand 10 as well as of the first carriage 15, is integrated in both the first carriage 15 and the second carriage 16.

Figure 7:
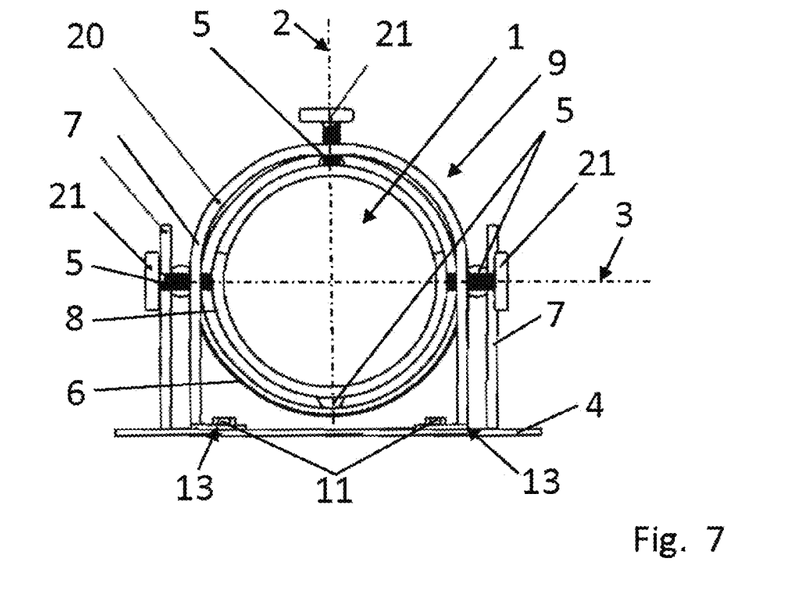
FIG. 7 is a front view of a third embodiment of a gas detection device according to the present invention.
Figure 8:
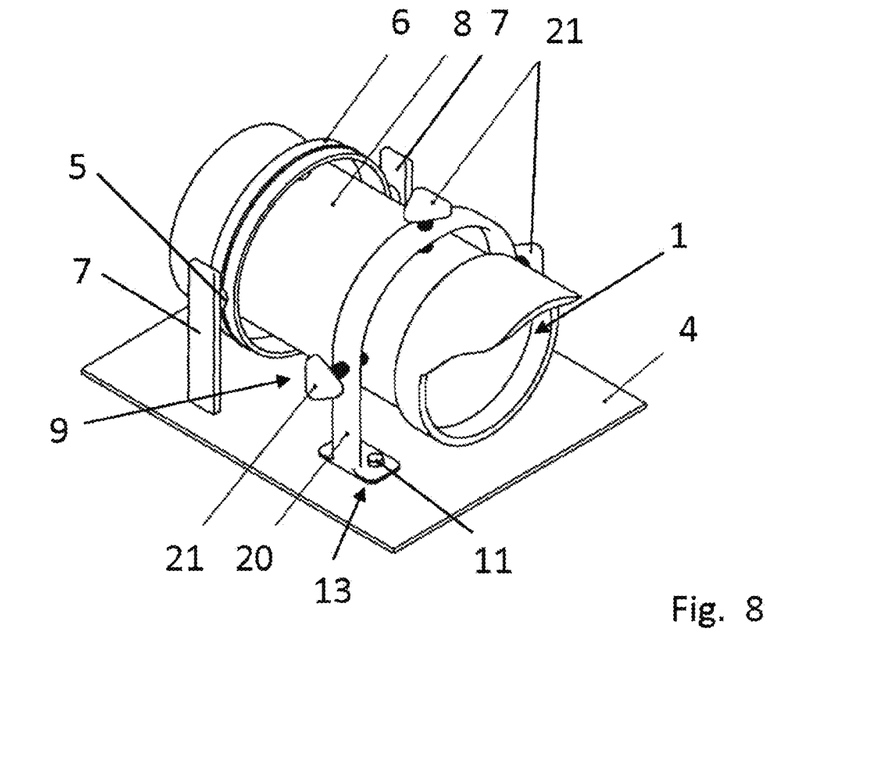
FIG. 8 is a perspective view of the gas detection device according to FIG. 7.

FIGS. 7 and 8 show an embodiment of an adjusting device 9 having an especially simple design for a gas detection device that otherwise corresponds to the exemplary embodiments according to FIGS. 1 through 6.

The adjusting device 9 comprises a strap-shaped frame 20, whose two free ends form feet 13, which are connected with the baseplate 4 via detachable fastening elements of the fastening device, in the form of fastening screws 11, which pass through passage openings of the frame 20 and mesh with threads of the baseplate 4. The frame 20 spans over the corresponding section of the housing 8 of the functional device 1 at a sufficiently great distance in order to make possible the pivoting of the functional device 1 in a defined pivoting range. At three points, the frame 20 forms internal threads, into which adjusting screws 21 are screwed. By rotating the adjusting screws 21, these can be moved in the direction of the housing 8 of the functional device 1 or away from same. Two of the three adjusting screws 21 are oriented coaxially. This pair of adjusting screws 21 thus forms a common (here horizontal) axis of motion, which is directed in parallel to the second pivot axis 3 and hence at right angles to the first pivot axis 2 of the bearing arrangement. The functional device 1 can be pivoted about the first pivot axis 2 by screwing in one adjusting screw 21 and unscrewing the other adjusting screw 21 of this pair simultaneously.

Pivoting of the functional device 1 about the second pivot axis 3 can be brought about by screwing in or unscrewing the third, central adjusting screw 21, whose axis of motion is directed at right angles to the axis of motion of the other adjusting screw 21. To ensure contact at all times between the contact end of the central adjusting screw 21 and the housing 8 of the functional device 1, provisions may be made for the housing 8 to be acted on by means of a spring element, whose spring force brings about a pivoting motion about the second pivot axis 3 in the direction of the central adjusting screw 21 (insofar as permitted by this) (not shown). It is likewise possible to provide a fixation between the central adjusting screw 21 and the housing 8, which fixation is detachable, allows a relative rotation, and can also transmit tensile forces besides forces of pressure (the same adjusting screw 21 can pull and push the functional device 1).

Provisions may also be made in another embodiment, not shown, for the frame 20 to be additionally provided with a strap, which surrounds the lower half of the housing 8 and in which a fourth adjusting screw, which is arranged coaxially with the upper, central adjusting screw 21, is integrated. Pivoting of the functional device 1 about the second pivot axis 3 could now be brought about by screwing these adjusting screws 21 in and out simultaneously, such as this is also provided for in the exemplary embodiment according to FIGS. 7 and 8 for pivoting about the first pivot axis 2.

Figure 9:
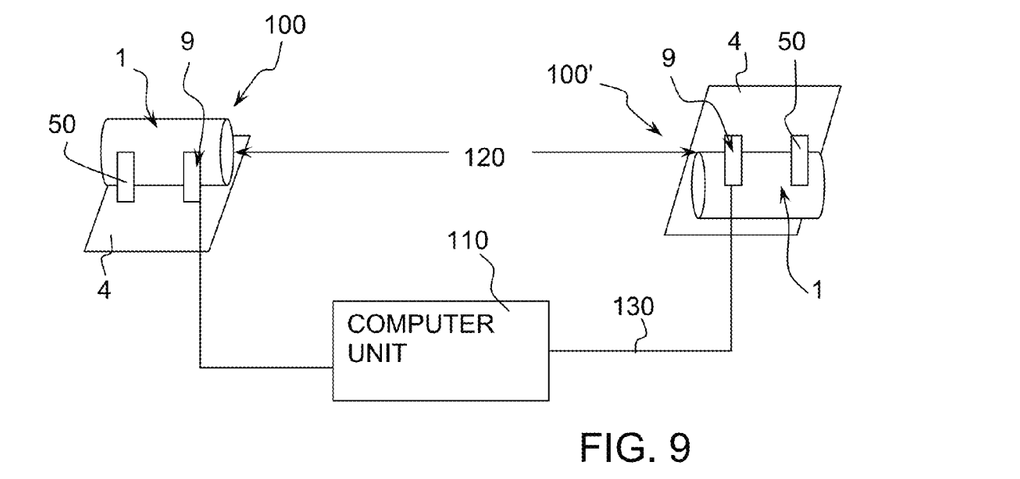
FIG. 9 is a schematic view showing two functional devices at ends of a defined measuring section.

FIG. 9 shows a detection unit 100 at a platform 4 at a first location and another detection unit 100' is shown at a platform 4 that is at a second location. The platforms 4 are shown with different orientations, but the particulars as to each platform 4 are not important in the schematic showing. The locations of the platforms 4 are spaced apart and are at ends of a measuring section 120. The functional unit 1 of the detection unit 100 is a transmitter and the functional unit 1 of the detection unit 100' is a receiver. Each detection units 100 and 100' is supported by a pivot arrangement 50 comprising pivot bearings 5, bearing ring 6 and beams 7 as described with reference to FIGS. 1-8. Each of the detection units 100 and 100' has an adjusting device 9 as shown in 4-6. The adjusting device 9 is shown with a connected computer unit 110, which may be used as a control device for the automatic orientation of the functional device 1 as a function of the adjusting deviation determined. The orientation of the functional units 1 is established by controlling the adjusting actuators (servo motors) of the adjusting device 9. As noted above, the connection 130 may be a wired or wireless connection and the computer 110 may instead be integrated in or attached with the adjusting device 9 or the functional unit 1. Also, as mentioned, only one adjusting device 9 may be used to establish the orientation of the functional device 1 of the detection unit 100 at the first location and the same adjusting device 9 may be used to establish the orientation of the functional device 1 of the detection unit 100' at the second location.

Figure 10:
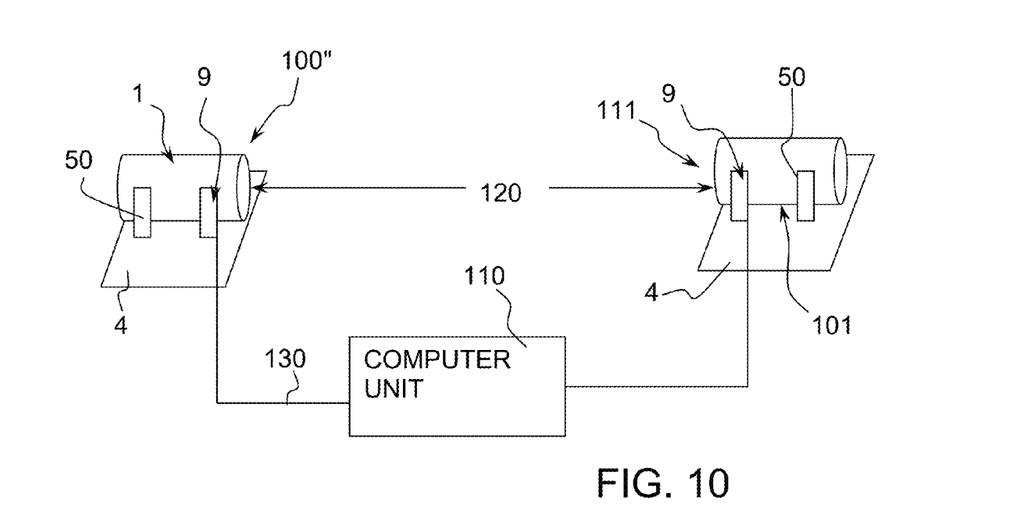
FIG. 10 is a schematic view showing two functional devices at ends of a defined measuring section.

FIG. 10 shows a configuration of detection units at a defined measuring section 120 that is similar to the configuration shown in FIG. 9. However, in FIG. 10, the detection unit 100" has a functional unit 1 that is a transmitter/receiver that interacts with a detection unit 111 that has a functional unit 101 that is a reflector.

While specific embodiments of the invention have been shown and described in detail to illustrate the application of the principles of the invention, it will be understood that the invention may be embodied otherwise without departing from such principles.

APPENDIX

| List of Reference Numbers | |
|---|---|
| 1 | Functional device |
| 2 | First pivot axis |
| 3 | Second pivot axis |
| 4 | Baseplate |
| 5 | Pivot bearing |
| 6 | Bearing ring |
| 7 | Beam |
| 8 | Housing |
| 9 | Adjusting device |
| 10 | Stand |
| 11 | Fastening screw |
| 12 | Adjusting screw |
| 13 | Foot of stand |
| 14 | Head of stand |
| 15 | First carriage |
| 16 | Second carriage |
| 17 | Rotary knob |
| 18 | Toothed gear |
| 19 | Toothed rack contour |
| 20 | Frame |
| 21 | Adjusting screw |
| 22 | Guiding projection |
| 23 | Spring shackle |
| 50 | Pivot mount arrangement |
| 100, 100' 100" | Detection unit |
| 101 | Functional device (reflector) |
| 111 | Detection unit (with reflector) |
| 110 | Computer unit |
| 120 | Measuring section |
| 130 | connection |

What is claimed is:

1. A gas detection device comprising:
a platform;
a functional device fixed pivotably to the platform for pivoting about at least two pivot axes relative to the platform, said pivot axes being oriented perpendicularly to one another, the functional device comprising at least one of a radiation emitter, a radiation receiver and a radiation reflector, the radiation varying in an analyzable manner due to a presence of a detectable gas; and an adjusting device comprising a fixing device for a temporary fixation to the platform and an application device for a defined application of forces to the functional device that lead to a pivoting about the pivot axes, said application device releasably engaging said functional device, said application device comprising a first adjusting element and a second adjusting element, said first adjusting element and said second adjusting element being configured such said first adjusting element generates a first adjusting line of generated force application in a direction perpendicular to one of said pivot axes and said second adjusting element generates a second adjusting element line of generated force application in a direction perpendicular to another one of said pivot axes.

2. A gas detection device in accordance with claim 1, wherein the functional device is a first functional device and further comprising a second functional device wherein the first functional device comprises a radiation emitter and the second functional device comprises a radiation receiver, which are each fixed on a respective platform.

3. A gas detection device in accordance with claim 1, wherein the functional device comprises radiation emitter and receiver; and further comprising a reflector positioned independently from the functional device.

4. A gas detection device in accordance with claim 1, wherein:
the application devices designed such that said first adjusting line of generated force application is located at a distance between 10 mm and 300 mm from said one of said pivot axes and said second adjusting line of generated force application is located at a distance between 10 mm and 300 mm from the another one of said pivot axes.

5. A gas detection device in accordance with claim 1, wherein the application device comprises a first carriage guided displaceably by said first adjusting element in a stand and a second carriage guided displaceably by said second adjusting element on the first carriage, said first adjusting element being adjustable independent of movement of said second adjusting element and said second adjusting element being adjustable independent of movement of said first adjusting element.

6. A gas detection device in accordance with claim 1, wherein the adjusting device comprise at least said first adjusting element and said second adjusting element acting on opposite sides of the functional device.

7. A gas detection device in accordance with claim 1, wherein the application device comprise said first adjusting element and said second adjusting element in the form of at least one of adjusting screws and adjusting actuators.

8. A gas detection device in accordance with claim 1, further comprising a control device for determining an adjusting deviation from a desired orientation of the functional device.

9. A gas detection device in accordance with claim 8, wherein:
the application device comprise adjusting actuators; and
the control device is connected with the adjusting actuators of the application device in a signal-carrying manner to orient the functional device automatically as a function of an adjusting deviation determined.

10. A gas detection device comprising:
a functional device comprising at least one of a radiation emitter, a radiation receiver and a radiation reflector, the radiation varying in an analyzable manner due to a presence of a detectable gas;
a pivot mount arrangement mounting the functional device pivotably to a support platform for pivoting about at least two pivot axes relative to the platform; and
an adjusting device comprising a fixing device for a temporary fixation of the adjusting device relative to the platform and an application device for a defined application of forces to the functional device that lead to a pivoting of the functional device about the pivot axes, said pivot axes being directed at right angles to one another, said application device comprising a first adjusting element and a second adjusting element, said first adjusting element being configured to apply a first adjusting element force to the functional device with a first adjusting element line generated force application that is perpendicular to one of said pivot axes, said second adjusting element being configured to apply a second adjusting element force to the functional device with a second adjusting element line generated force application that is perpendicular to another one of said pivot axes.

11. A gas detection device in accordance with claim 10, wherein the functional device is a first functional device and further comprising:
a second functional device comprising at least one of a radiation emitter, a radiation receiver and a radiation reflector, the radiation varying in an analyzable manner due to a presence of a detectable gas; and
a second pivot mount arrangement fixing the second functional device pivotably to a support platform for pivoting about at least two pivot axes relative to the platform.

12. A gas detection device in accordance with claim 11, wherein:
the first functional device comprises a radiation emitter and a radiation receiver; and
the second functional device comprises a reflector positioned independently from the first functional device.

13. A gas detection device in accordance with claim 10, wherein:
the first adjusting element line generated force application is located at a distance between 10 mm and 300 mm from said one of said pivot axes and said second adjusting element line generated force application is located at a distance between 10 mm and 300 mm from said another one of said pivot axes.

14. A gas detection device in accordance with claim 10, wherein the application device comprises:
a first carriage guided displaceably by the first adjusting element in a stand, said first adjusting element and said second adjusting element being movable independent of movement of each other; and
a second carriage guided displaceably by the second adjusting element on the first carriage, said second carriage being movable independent of movement of said first carriage, said first carriage being movable independent of movement of said second carriage.

15. A gas detection device in accordance with claim 14, further comprising a control device wherein:
the first adjusting element comprises a first adjusting actuator;

the second adjusting element comprises a second adjusting actuator;

the control device controls the first adjusting actuator and the second adjusting actuator for a controlled orientation of the functional device.

the control device is connected with the adjusting actuators of the application device in a signal-carrying manner.

16. A gas detection device in accordance with claim 15, wherein the control device is configured to determine an adjusting deviation from a desired orientation of the functional device and to generate control signals to orient the functional device automatically as a function of an adjusting deviation determined.

17. A gas detection device in accordance with claim 10, wherein the application device comprise said first adjusting element and said second adjusting element in the form of at least one of adjusting screws and adjusting actuators.

18. A gas detection device in accordance with claim 10, further comprising:
  a bearing support structure comprising an inner bearing support structure surface and an outer bearing support structure surface;
  a first plurality of first bearings, each of said first plurality of first bearings being arranged between said inner bearing support structure surface and said functional device;
  a second plurality of second bearings;
  a first support element, one of said second bearings being arranged between said first support element and said outer bearing support structure surface;
  a second support element, another one of said second bearing being arranged between said second support element and said outer bearing support structure surface.

19. A gas detection device in accordance with claim 1, wherein the application device comprises:
  a first carriage guided displaceably by the first adjusting element in a stand, said first adjusting element being movable independent of movement of said second adjusting element, said second adjusting element being movable independent of movement of said first adjusting element; and
  a second carriage guided displaceably by the second adjusting element on the first carriage, said second carriage being movable in a direction of said functional element and in a direction away from said functional element independent of movement of said first carriage, said first carriage being movable independent of movement of said second carriage.

20. A gas detection device in accordance with claim 1, further comprising:
  a bearing support structure comprising an inner bearing support structure surface and an outer bearing support structure surface;
  a first plurality of first bearings, each of said first plurality of first bearings being arranged between said inner bearing support structure surface and said functional device;
  a second plurality of second bearings;
  a first support element, one of said second bearings being arranged between said first support element and said outer bearing support structure surface;
  a second support element, another one of said second bearing being arranged between said second support element and said outer bearing support structure surface.

* * * * *